United States Patent
Poley et al.

(10) Patent No.: US 6,418,924 B1
(45) Date of Patent: Jul. 16, 2002

(54) DRUG DELIVERY DEVICE

(75) Inventors: John Poley; Philip Seeney, both of Melbourn (GB)

(73) Assignee: P A Knowledge Limited, Grand Cayman, KY (US)

( * ) Notice: Subject to any disclaimer, the term of this patent is extended or adjusted under 35 U.S.C. 154(b) by 0 days.

(21) Appl. No.: 09/554,688

(22) PCT Filed: Nov. 16, 1998

(86) PCT No.: PCT/GB98/03451

§ 371 (c)(1), (2), (4) Date: Jul. 14, 2000

(87) PCT Pub. No.: WO99/25404

PCT Pub. Date: May 27, 1999

(30) Foreign Application Priority Data

Nov. 18, 1997 (GB) ............................................. 9724223

(51) Int. Cl.$^7$ ............................................. A61M 11/00
(52) U.S. Cl. ........................... 128/200.14; 128/200.17; 128/200.18; 128/203.12; 128/203.15
(58) Field of Search ....................... 128/203.12, 203.15, 128/200.14, 200.17, 200.18; 604/58, 247

(56) References Cited

U.S. PATENT DOCUMENTS

| | | | | |
|---|---|---|---|---|
| 4,778,451 A | * | 10/1988 | Kamen | ......................... 604/67 |
| 4,808,161 A | * | 2/1989 | Kamen | ......................... 604/67 |
| 4,826,482 A | * | 5/1989 | Kamen | ......................... 604/67 |
| 4,976,162 A | * | 12/1990 | Kamen | ....................... 73/865.9 |
| 5,088,515 A | * | 2/1992 | Kamen | .......................... 137/15 |
| 5,116,021 A | * | 5/1992 | Faust et al. | .............. 251/149.1 |
| 5,211,201 A | | 5/1993 | Kamen et al. | |
| 5,284,133 A | | 2/1994 | Burns et al. | |
| 5,339,990 A | | 8/1994 | Wilder | |
| 5,497,944 A | * | 3/1996 | Weston et al. | ............... 239/321 |

FOREIGN PATENT DOCUMENTS

| | | |
|---|---|---|
| EP | 0 372 863 | 6/1990 |
| EP | 0 569 611 | 11/1993 |
| GB | 2 083 569 | 3/1982 |

* cited by examiner

Primary Examiner—John G. Weiss
Assistant Examiner—Darwin Erezo
(74) Attorney, Agent, or Firm—Jacobson Holman, PLLC

(57) ABSTRACT

A drug delivery device for the delivery of a fluid carrying or including a therapeutic agent. The device including a reservoir for storing the fluid, and in fluid connection therewith a regulatable pump for dispensing the fluid via an outlet. A control device is further provided, for selectively controlling the pumping mode of the pump such that in a first mode the pump acts to dispense the fluid and in a second mode the pump acts such that substantially no fluid is dispensed.

9 Claims, 1 Drawing Sheet

DRUG DELIVERY DEVICE

FIELD OF THE INVENTION

The invention relates to a control means for a drug delivery device and also a drug delivery device including a control means.

BACKGROUND OF THE INVENTION

A number of therapeutic treatments are administered by inhalation and thus, primarily, are directed to the upper respiratory tract ie the nose and throat. Accordingly, a number of conventional devices exist for this purpose. In some instances, for example where a therapeutic agent may be dangerous when a given dose is exceeded, or alternatively where a therapeutic agent may be potentially addictive, it is important to regulate the administered dose or dose regime. It is therefore important to try and prevent the inadvertent overdosing of a given therapeutic agent or the inadvertent addiction to a given therapeutic agent.

Conventional dispensers typically include a dispensing means which controls the amount of therapeutic agent delivered per use, or application, of the dispense. For example, a pump and associated chamber can be used to control the delivery of a selected amount of therapeutic agent, typically in the form of a therapeutic fluid, thus the volume of fluid dispensed is determined by the geometry of the chamber on which the pump acts and therefore for each pumping action a given volume of fluid is dispensed. In this provided an individual only uses the dispenser, or pump, a specified number of times over a given period, the dose of therapeutic agent should fall within a dose regime.

However, it is not uncommon for individuals to forget how much of a given quantity of therapeutic agent has been inhaled in any given period and therefore to inadvertently exceed a dosage. Additionally, given that pump operated dispensers sometimes need to be primed for a correct amount of therapeutic agent to be dispensed an individual may not receive a correct dosage of therapeutic agent. And indeed in these circumstances it is possible for an individual to inadvertently exceed his or her recommended dose by following this partial dose, with a full dose and thus run the risk of inadvertent overdose or addiction.

A further complication concerns the fact that increasingly new and effective therapeutic agents are becoming hazardous and therefore if a partial dose, due to inadequate priming, is not taken it is not always advisable to simply dispense into the atmosphere by a technique known as air priming the partial dose. Additionally, it is not always advisable to air prime because of the considerable expense that may be associated with the use of certain therapeutic agents in this way.

It can therefore be seen that there is a need to provide a means for controlling the dispensing of therapeutic agents; and a device including same.

SUMMARY OF THE INVENTION

It is therefore an object of the invention to provide a control means in, or for use in a dispensing device whereby the dose regime of a dispensed therapeutic can be reliably controlled.

According to a first aspect of the invention there is provided a drug delivery device for the delivery of a fluid carrying or, comprising a therapeutic agent said device comprising: a reservoir for storing said fluid, and in fluid connection therewith a regulatable pump means for dispensing said fluid via an outlet means; wherein a control means is further provided for selectively controlling the pumping mode of said pump means such that in a first mode said pump means acts to dispense said fluid and in a second mode said pump means acts such that substantially no fluid is dispensed.

In a preferred embodiment of the invention said reservoir comprises an exit portion comprising a dispensing chamber and associated dispensing channel which is in fluid connection with a storage portion of said reservoir.

In a preferred embodiment of the invention said pump means comprises a selectively controllable bypass valve which has a dual mode of operation. In a first mode when the bypass valve is closed fluid in said reservoir can be dispensed from said device. Alternatively, or additionally, in a second mode when said bypass valve is opened fluid in said reservoir is diverted from an exit portion of said reservoir to a storage portion of said reservoir.

More preferably still said bypass valve comprises an aperture covered by a flexibly membrane that allows the passage therethrough or thereby of therapeutic fluid when said bypass valve is in said second mode.

In yet a further preferred embodiment of the invention said bypass valve comprises an aperture in said dispensing chamber and/or said dispensing channel and a means for releasably sealing same such that when the device is to dispense a dosage of therapeutic agent said aperture is closed; and when the device is to prevent dispensing of said therapeutic agent the aperture of the bypass valve is opened thus enabling therapeutic agent in said dispensing chamber to be diverted to the storage portion of said reservoir. Ideally, said releasable sealing means comprises an urging means which is ideally controlled using electrical means, and most ideally comprises a solenoid.

It will therefore be apparent that when the urging means acts so as to apply sufficient pressure to the releasable sealing means the aperture in the dispensing chamber is sealed and this ensures that therapeutic agent can be dispensed from the device. Alternatively, when the urging means does not act to apply sufficient pressure to the releasable sealing means the aperture in the dispensing chamber is opened and the therapeutic agent is therefore directed towards the reservoir storage portion.

It therefore follows that the selective control of the urging means status will determine the pumping mode of the pump and so the ability of the deliverer device to dispense medication.

In yet a further preferred embodiment of the invention control means ideally in the form of an electronic circuit with at least one microchip is provided so that the number of times the device can dispense a therapeutic agent can be controlled over a set period of time. Additionally, and advantageously, said control means is adapted to record information relating to use of the dispensing device and also to respond to interrogation of same so that, with the provision and use of a suitable display means, an individual can enquire as to how frequently the device may be used over a remaining period of time or how much medication has already been administered. Additionally further still an interface means is provided whereby data stored on said control means can be down-loaded to another compatible device for further use/analysis. This is useful for determining drug regime compliance either from the perspective of a GP or clinical trials coordinator.

An additional advantage intrinsic in the device of the invention concerns an ability to prime the pump means without dispensing the therapeutic agent. As will be well known to those skilled in the art, the loss of prime in pumps is a consequence of fluid leaking out of the relevant chamber, in this instance the dispensing chamber. This typically occurs when the device is jostled or laid on its side. Thus the amount of fluid in the dispensing chamber is decreased and an insufficient dose is administered on use. In order to ensure that a correct dose is administered the conventional device is repeatedly operated at least once, to refill the dispensing chamber. This involves effecting additional cycles of the device and thus dispensing some therapeutic agent to the atmosphere. However with the device of the invention it is possible to prime the pump with the bypass valve open and thus divert the therapeutic fluid in the dispensing chamber to the reservoir storage portion. In this way, the device can be primed without loss of medication or fluid.

It therefore follows that the control means could be further programmed to enable a user to prime the device each time before usage. For example, it is possible to program the control means so that at least one pump operation is provided, for the purpose of priming with the bypass valve open, and then a further pump operation is provided with the bypass valve closed so as to ensure that on a selected pump operation the device dispenses a desired amount of therapeutic agent.

It can therefore be seen that the device of the invention not only enables one to control the number of times a therapeutic agent is dispensed from the device but also it enables repriming without the disadvantages associated with air priming.

According to a second aspect of the invention there is provided a drug delivery device for the delivery of the fluid carrying or comprising a therapeutic agent. The said device comprising: a reservoir for storing said fluid, and in fluid connection therewith a regulatable pump means for dispensing said fluid via an outlet means; wherein a primer control means is further provided for selectively controlling the pumping mode of said pump means such that in a first mode said pump means acts to dispense said fluid and in a second mode said pump means acts to return fluid to said reservoir.

A single embodiment of the invention will now be described by way of example only. It is notable that this single embodiment is not intended to limit the scope of the application but merely serve for the purpose of comprehension.

BRIEF DESCRIPTION OF THE DRAWINGS

The embodiment of the invention will be described with reference to the single FIGURE which is a part sectional, part peeled-back, perspective view of a device in accordance with the invention.

DETAILED DESCRIPTION OF THE PREFERRED EMBODIMENTS

Figure 1:
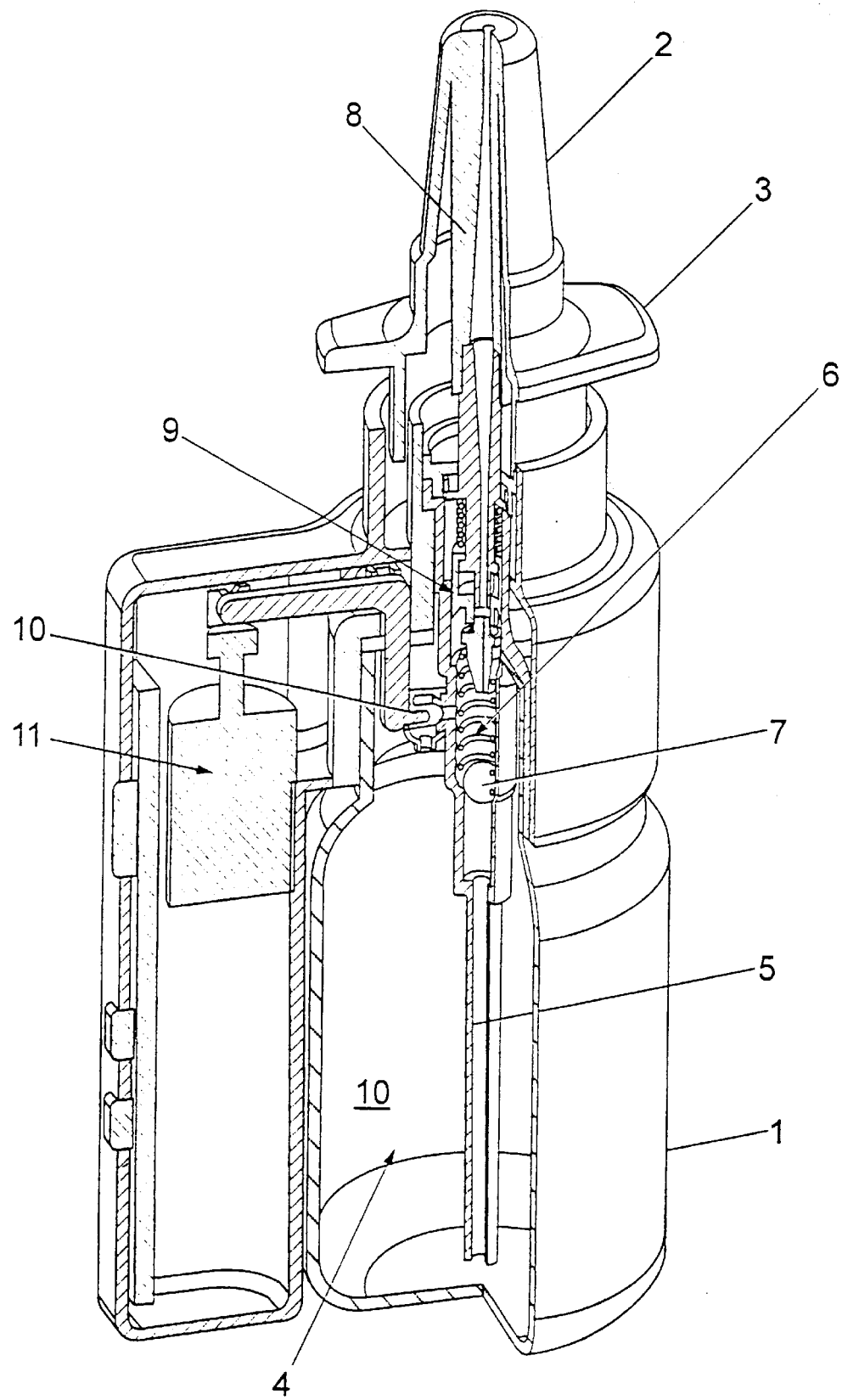

The device comprises a generally cylindrical body member attached to a dispensing nozzle 2 in conventional manner. Nozzle is provided with an actuator member 3 which is adapted to enable a user to apply pressure thereto using the fingers of one hand. The lower part of body 1 comprises a storage reservoir 4 into which a selected volume of therapeutic fluid can be stored. Centrally located in reservoir 4 there is provided a cylindrical dispensing channel 5 which communicates with, and is in fluid connection with, a dose regulation chamber 6 via a releasable ball closure means 7. Dose regulation chamber 6 s in fluid connection with dispensing channel 8 upon depression of breakback piston 9 as will be described hereinafter. Dispensing channel 8 terminates at the outermost tip of nozzle 2. This arrangement ensures that the fluid stored in reservoir 4 travels through the device to be dispensed via nozzle 2.

Notably, the dimensions of dose regulation chamber 6 and dispensing channel 8 determine the dosage of fluid dispensed upon operation of the device. Thus the dimensions are suitably selected for a given concentration of therapeutic fluid. Or, alternatively, the concentration of a given therapeutic fluid is determined having regard to the dimensions of said dose regulation chamber 6 and channel dispensing means 8.

Actuator 3 is operatively connected to breakback piston 9 in conventional manner such that the depression of actuator 3 results in the downward movement of breakback piston 9. As piston 9 is moved downwardly it travels into the dose regulation chamber 6 and the pressure in same increases until what is known as a break pressure is reached. At this point part of the piston assembly breaks away thus ensuring that the dose regulation chamber 6 is in fluid connection with the dispensing channel 8 and the pressurised fluid then exits the dispensing device.

The exact arrangement for ensuring fluid connection between dose regulation chamber 6 and dispensing channel 8 can be selected from conventional devices, including permutations or variations thereof, and is not intended to limit the scope of the application.

Indeed, the exact arrangement of the pumping mechanism may be selected from conventional devices, including permutations or variations thereof, and is not intended to limit the scope of the application.

In the device of the invention the dose regulation chamber 6 or, alternatively, the dispensing channel 8 is provided with a bypass valve 10. Bypass valve 10 comprises a cavity provided in the wall of the dose regulation chamber 6 and a releasable closure means in contact therewith. In a preferred embodiment of the invention the releasable enclosure means comprises a flexible (or resilient) covering for the aperture typically in the form of a flexible (or resilient) band which is placed about the outer surface of the dose regulation chamber 6 and also an associated urging means which can be made to selectively press against the releasable band ideally in the region of the aperture. In the embodiment of the invention shown in the FIGURE the releasable urging means comprises a solenoid 11 which can be activated/deactivated, depending on the configuration of the solenoid so as to press against the resilient band. However, in an alternative mode of operation the deactivation/activation of the solenoid will have the opposite effect and the urging member of the solenoid will be positioned remote from the resilient band enabling fluid to escape from dose regulation chamber 6 when a given pressure is reached. Clearly the flexibility or resilience of the band is selected with this in mind. In alternative embodiments of the invention more than one bypass valve may be provided or alternatively at least one bypass valve is provided in either or both the dose regulation chamber 6 or the dispensing channel 8.

The dispensing device is suitably provided with an electronic circuit means (not shown) which can be programmed to control the operation of said bypass valve in accordance with the dispensing requirements of the device. Additionally, display means (not shown) may be provided so that information stored can be viewed by a user. Additionally, and advantageously, the electronics may be programmed for interrogation so that a user may enquire as to the status of the device or the number of doses dispensed over a given period of time and thus the remaining number of doses to be dispensed over a given period of time or indeed any other information that may be beneficial to the successful use of the device. Additionally, interface means may be provided so that the device can be used in association with other equipment for the purpose of data analysis.

Typically therefore, in use, the device is filled with an appropriate amount of selected therapeutic fluid and the electronics is programmed so that, for example the bypass valve is opened for at least one operation of the pump and closed for the next subsequent permitted operation thus ensuring that a full dose of therapeutic fluid is dispensed on the selected operation of the pump. Additionally, a timer may be incorporated into the electronics so that the bypass valve remains open for a predetermined time interval so that in this predetermined time interval although the pump may be operated no medication is dispensed. Once a predetermined time interval has elapsed the electronics are programmed so that following priming of the pump on subsequent operation of the pump a dosage of therapeutic fluid is dispensed if permitted. Thus in this way, at the correct time interval, the user is able to operate the pump at least once in order to prime same and then operate the pump a further time in order to dispense a reliable amount of medication. The aforementioned cycle of the working of the device can be repeated for a given number of times or alternatively, the predetermined time interval may be varied accordingly to a user's requirements so as to provide for a constant and repeatable cycle of medication dispensing or a variable cycle of medication dispensing.

It can therefore be seen that the invention concerns a novel dispensing means for controlling the administration of a therapeutic agent.

What is claimed is:

1. A drug delivery device for delivery of a fluid carrying or comprising a therapeutic agent said device comprising: a reservoir for storing said fluid, and in fluid connection therewith a regulatable pump means for dispensing said fluid via an outlet means; wherein a control means is further provided for selectively controlling a pumping mode of said pump means such that in a first mode said pump means acts to dispense said fluid and in a second mode said pump means acts such that substantially no fluid is dispensed wherein said pump means is primed in said second mode such that the device can be primed without loss of medication of fluid,
said pump means including a selectively controllable bypass valve which has a dual mode of operation,
in a second mode when said bypass valve is opened, fluid in said reservoir is diverted from an exit portion of said reservoir to a storage portion of said reservoir,
said bypass valve including, an aperture covered by a flexible membrane allowing the passage therethrough or thereby of therapeutic fluid when said bypass valve is in said second mode.

2. A drug delivery device according to claim 1 wherein said reservoir comprises an exit portion comprising a dispensing chamber and associated dispensing channel which is in fluid connection with a storage portion of said reservoir.

3. The drug delivery device as claimed in claim 1 wherein in a first mode when the bypass valve is closed fluid in said reservoir can be dispensed from said device.

4. The drug delivery device as claimed in claim 1 said control means is provided so that the number of times the device can dispense a therapeutic agent can be controlled over a set period of time.

5. The drug delivery device as claimed in claim 4 wherein said control means is provided in the form of an electronic circuit.

6. The drug delivery device as claimed in claim 1, wherein said control means is adapted to record information relating to use of the dispensing device and also to respond to interrogation of the dispensing device.

7. The drug delivery device as claimed in claim 1 an interface means is provided whereby data stored on said control means can be downloaded to another compatible device for further use/analysis.

8. A drug delivery device as claimed in claim 1 wherein the control means is adapted to be programmed so that at least one pump action operation is provided, for the purpose of priming with the bypass valve open, and then a further pump operation is provided with the bypass valve closed so as to ensure that on a selected pump operation the device dispenses a desired amount of therapeutic agent.

9. A drug delivery device for delivery of a fluid carrying or comprising a therapeutic agent said device comprising: a reservoir for storing said fluid, and in fluid connection therewith a regulatable pump means for dispensing said fluid via an outlet means; wherein a control means is further provided for selectively controlling a pumping mode of said pump means such that in a first mode said pump means acts to dispense said fluid and in a second mode said pump means acts such that substantially no fluid is dispensed wherein said pump means is primed in said second mode such that the device can be primed without loss of medication of fluid,
said pump means including a selectively controllable bypass valve which has a dual mode of operation,
said bypass valve comprises an aperture in at least one of said dispensing chamber and said dispensing channel and a means for releasably sealing the at least one of the dispensing chamber and the dispensing channel such that when the device is to dispense a dosage of therapeutic agent said aperture is closed; and when the device is to prevent dispensing of said therapeutic agent the aperture of the bypass valve is opened thus enabling therapeutic agent in said dispensing chamber to be diverted to the storage portion of said reservoir.

* * * * *